(12) United States Patent
Astilla et al.

(10) Patent No.: US 8,679,193 B2
(45) Date of Patent: Mar. 25, 2014

(54) AMPUTATION RESIDUUM DEVICE AND METHOD OF USING THE SAME

(75) Inventors: Michael Joseph Astilla, Durham, NC (US); Laura Brewer Riedel, Durham, NC (US)

(73) Assignee: Pando Innovations, Durham, NC (US)

( * ) Notice: Subject to any disclaimer, the term of this patent is extended or adjusted under 35 U.S.C. 154(b) by 57 days.

(21) Appl. No.: 13/398,521

(22) Filed: Feb. 16, 2012

(65) Prior Publication Data

US 2012/0209404 A1 Aug. 16, 2012

Related U.S. Application Data

(60) Provisional application No. 61/443,552, filed on Feb. 16, 2011.

(51) Int. Cl.
*A61F 2/60* (2006.01)

(52) U.S. Cl.
USPC .......................................................... 623/33

(58) Field of Classification Search
USPC ..................................... 623/32–37
See application file for complete search history.

(56) References Cited

U.S. PATENT DOCUMENTS

| | | | |
|---|---|---|---|
| 3,945,046 A | 3/1976 | Stromgren | |
| 4,139,002 A | 2/1979 | Almedia | |
| 4,842,608 A | 6/1989 | Marx et al. | |
| 4,872,879 A | 10/1989 | Shamp | |
| 4,981,132 A | 1/1991 | Chong | |
| 5,211,667 A | 5/1993 | Danforth | |
| 5,301,370 A | 4/1994 | Henson | |
| 5,385,534 A | 1/1995 | Cassford | |
| 5,507,722 A | 4/1996 | Richardson | |
| 5,529,575 A | 6/1996 | Klotz | |
| 5,571,209 A | 11/1996 | Brown, Sr. | |
| 5,653,766 A | 8/1997 | Naser | |
| 6,406,499 B1 | 6/2002 | Kania | |
| 6,793,682 B1 | 9/2004 | Mantelmacher | |
| 6,991,657 B1 | 1/2006 | Price, Jr. | |
| 7,641,625 B2 | 1/2010 | Nobbe | |
| 7,867,286 B2 * | 1/2011 | Einarsson | ....................... 623/33 |
| 2010/0036505 A1 | 2/2010 | Hassler | |
| 2010/0191348 A1 | 7/2010 | Kettwig et al. | |

FOREIGN PATENT DOCUMENTS

| | | |
|---|---|---|
| FR | 2512666 | 3/1983 |
| GB | 2103490 A | 2/1983 |
| GB | 2435216 A | 8/2007 |

* cited by examiner

*Primary Examiner* — Bruce E Snow
(74) *Attorney, Agent, or Firm* — Esther F. Queen; Moore & Van Allen PLLC (57) ABSTRACT

An apparatus and method for post amputation residuum maintenance and for preserving motion of the knee are provided. The apparatus includes an elongated shell having a longitudinal axis and defining a hollow interior closed at a distal end, the shell having an opening extending from a proximal end and adapted to receive a residuum into the interior of the shell, and a longitudinal slit having a circular aperture at each end.

4 Claims, 11 Drawing Sheets

AMPUTATION RESIDUUM DEVICE AND METHOD OF USING THE SAME

CROSS-REFERENCE TO RELATED APPLICATION

This application claims priority to U.S. Provisional Application No. 61/443,552 entitled "Post Amputation Residuum Maintenance and Knee Range of Motion Preservation Apparatus" filed on Feb. 16, 2011, the entire contents of which are incorporated by reference herein.

BACKGROUND

Following amputation, edema often occurs in the amputated region causing volume fluctuations in the residuum. It is often important to stabilize the residuum by apply compression to the residuum. The residuum may be placed in a splint or other device to manage swelling and protect the residuum. Current devices are formed from a continuous piece of plastic to form the posterior and anterior portions and a distal end, where the anterior and posterior portions are attached, such that variances in volume are not appropriately accommodated at the distal end of the residuum.

For all these reasons and others, there is a need for an improved user-friendly device and method for accommodating residuum volume fluctuations.

SUMMARY

Embodiments an amputation residuum device and method of using the same are described herein which address these and/or other. In some embodiments, the amputation residuum device comprises a posterior shell having longitudinal slits formed therein and a multidurometer, soft pre-tibial shell is provided. The residuum device provides for a limb volume and diameter variance accommodation via the floating pre-tibial shell and the flexible posterior shell.

In some embodiments, an apparatus for post amputation residuum maintenance is provided. The apparatus includes: an elongated shell having a longitudinal axis and defining a hollow interior closed at a distal end, the shell having an opening extending from a proximal end and adapted to receive a residuum into the interior of the shell, and a longitudinal slit having a circular aperture at each end.

In some embodiments of the apparatus, the shell further includes a second slit extending parallel to at least a portion of the longitudinal slit. In other embodiments, a distal end of the longitudinal slit is defined by the closed distal end of the shell. In still other embodiments, the shell has a second slit having a distal end defined by the closed distal end of the shell. In some embodiments, the distal end of the longitudinal slit is positioned from about 0.5 inches to about 3 inches from the distal end of the second slit. In some embodiments, the apparatus includes a second shell adapted to be positioned adjacent to the residuum, the second shell configured to cover at least a portion of the opening of the shell. In some embodiments of the apparatus, the second shell has a longitudinal axis, and the second shell is substantially arcuate in a cross-section taken transverse to the longitudinal axis of the second shell.

In other embodiments, the apparatus further includes an inner foam layer comprising a soft material; and an outer foam layer comprising a rigid material, wherein the outer layer is positioned adjacent to the inner foam layer. In still other embodiments, the peripheral edge of the inner foam layer tapers outwardly. In further embodiments, the peripheral edge of the outer foam layer tapers inwardly.

In some embodiments of the apparatus, the shell has a circumference, and the opening is about 40% of the circumference of the shell. In other embodiments, the shell comprises a proximal portion and a distal portion, wherein the width of the opening defined by the distal portion is greater than the width of the opening defined by the proximal portion. In further embodiments, the apparatus further includes at least one enclosure panel; and a means for securing that at least enclosure panel to the shell. In other embodiments, the apparatus further includes a circular pad disposed in the interior of the shell adjacent the closed end.

In some embodiments, method for maintaining post amputation residuum maintenance is provided. The method includes: providing an elongated shell having a longitudinal axis and defining a hollow interior closed at a distal end, the shell having an opening extending from a proximal end and adapted to receive a residuum into the interior of the shell, and a longitudinal slit having a circular aperture at each end; and positioning a residuum in the interior of the shell via the opening. In other embodiments, the method further includes the step of providing a second shell adapted to be positioned adjacent to the residuum, the second shell configured to cover at least a portion of the opening. In still other embodiments, the method further includes the step of adjusting the position of the second shell to fit against the residuum, wherein at least a portion of an edge of the first shell defining the opening partially overlaps the second shell. In further embodiments, the method further includes trimming a portion of the second shell to accommodate the residuum exposed through the opening in the shell.

In some embodiments of the method, the shell has a second slit extending parallel to at least a portion of the longitudinal slit and a distal end of the longitudinal slit is defined by the closed distal end of the shell and wherein a distal end of the second slit is defined by the closed distal end of the shell. In other embodiments, the method further includes the step of positioning an enclosure panel over at least a portion of the residuum exposed through the opening in the shell; and securing the enclosure panel to the shell. In still other embodiments, the method further includes the step of modifying the dimensions of the shell to accommodate the residuum by trimming a portion of the first shell

BRIEF DESCRIPTION OF THE DRAWINGS

Having thus described embodiments of the invention in general terms, reference will now be made the accompanying drawings, wherein:

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Where possible, any terms expressed in the singular form herein are meant to also include the plural form and vice versa, unless explicitly stated otherwise. Like numbers refer to like elements throughout.

Embodiments described herein provide a device and method for amputation residuum maintenance. A device and method for stabilization of an amputation residuum while accommodating fluctuations in volume and diameter of the residuum are provided. It will be understood that the term "residuum" as used herein includes the remaining portion of an amputated body part, such as an amputated limb and, in particular, a leg. When used with a limb, such as a leg, the residuum device helps with knee range of motion preservation. The residuum device described herein may be used for human and animal residuum maintenance.

Figure 1A:
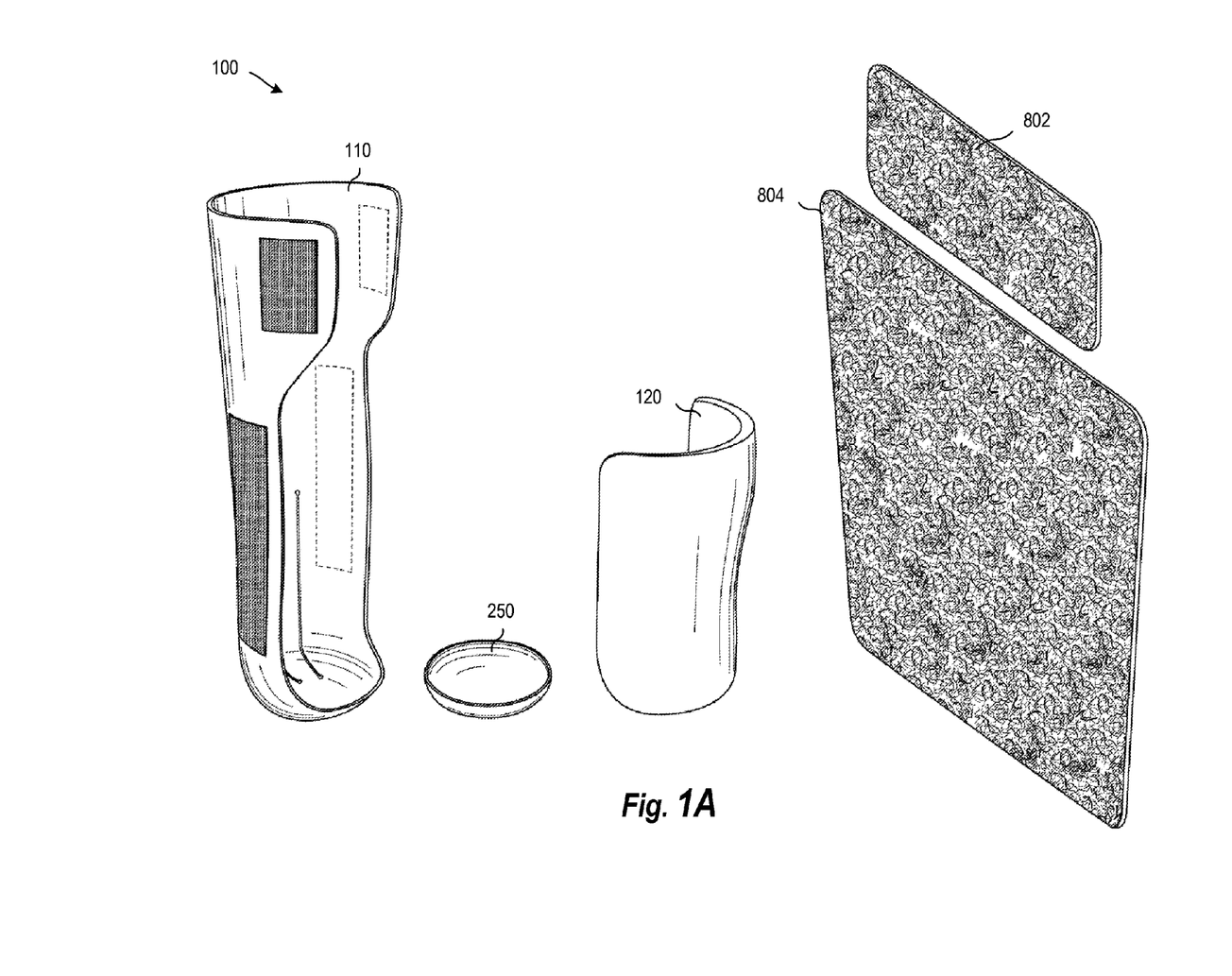
FIG. 1A is an exploded perspective view of an amputation residuum device according to some embodiments.
Figure 1B:
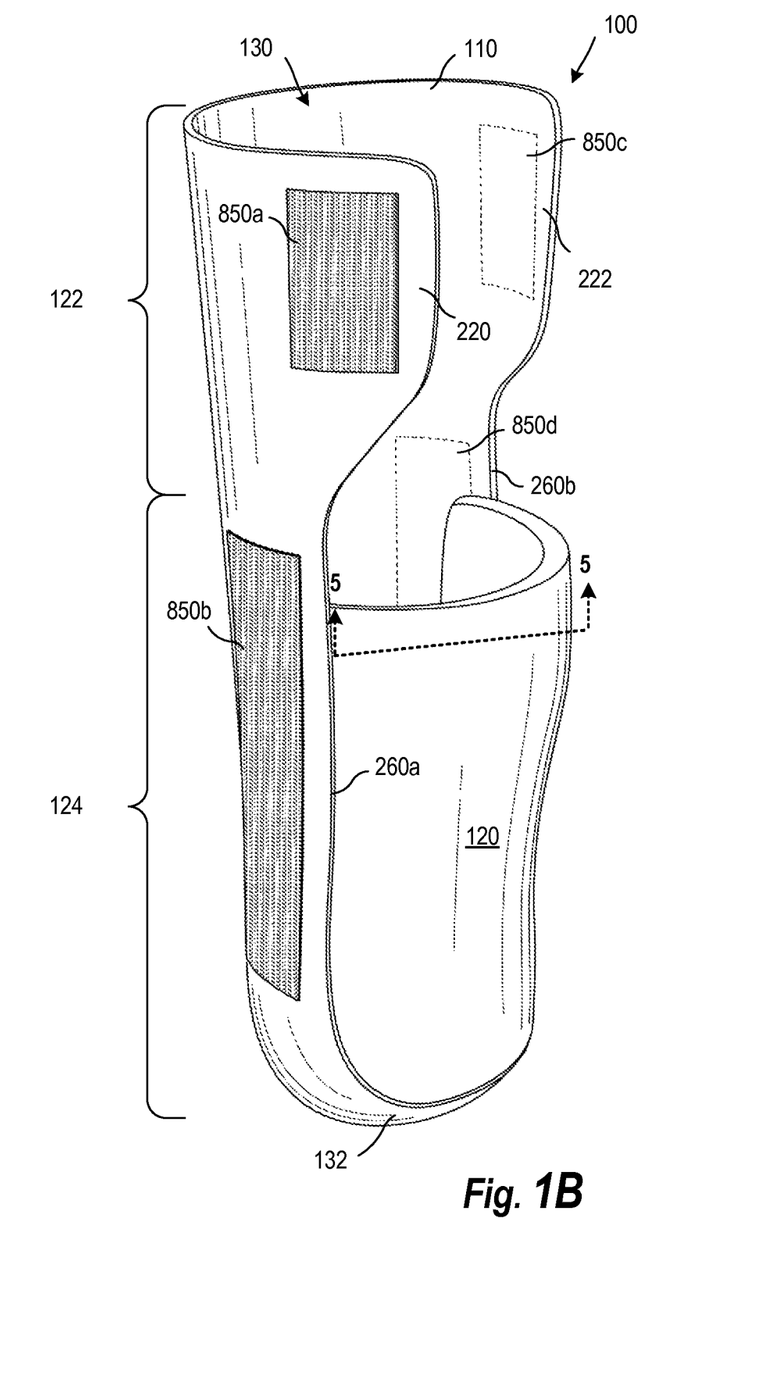
FIG. 1B is a perspective view of a partially assembled residuum device as shown in FIG. 1A.

Referring now to the figures, FIGS. 1A-1B illustrate one embodiment of an amputation residuum device 100. The residuum device 100 includes a posterior shell 110, a pre-tibial shell 120, enclosure panels 802, 804, and a circular pad 250.

Figure 2:
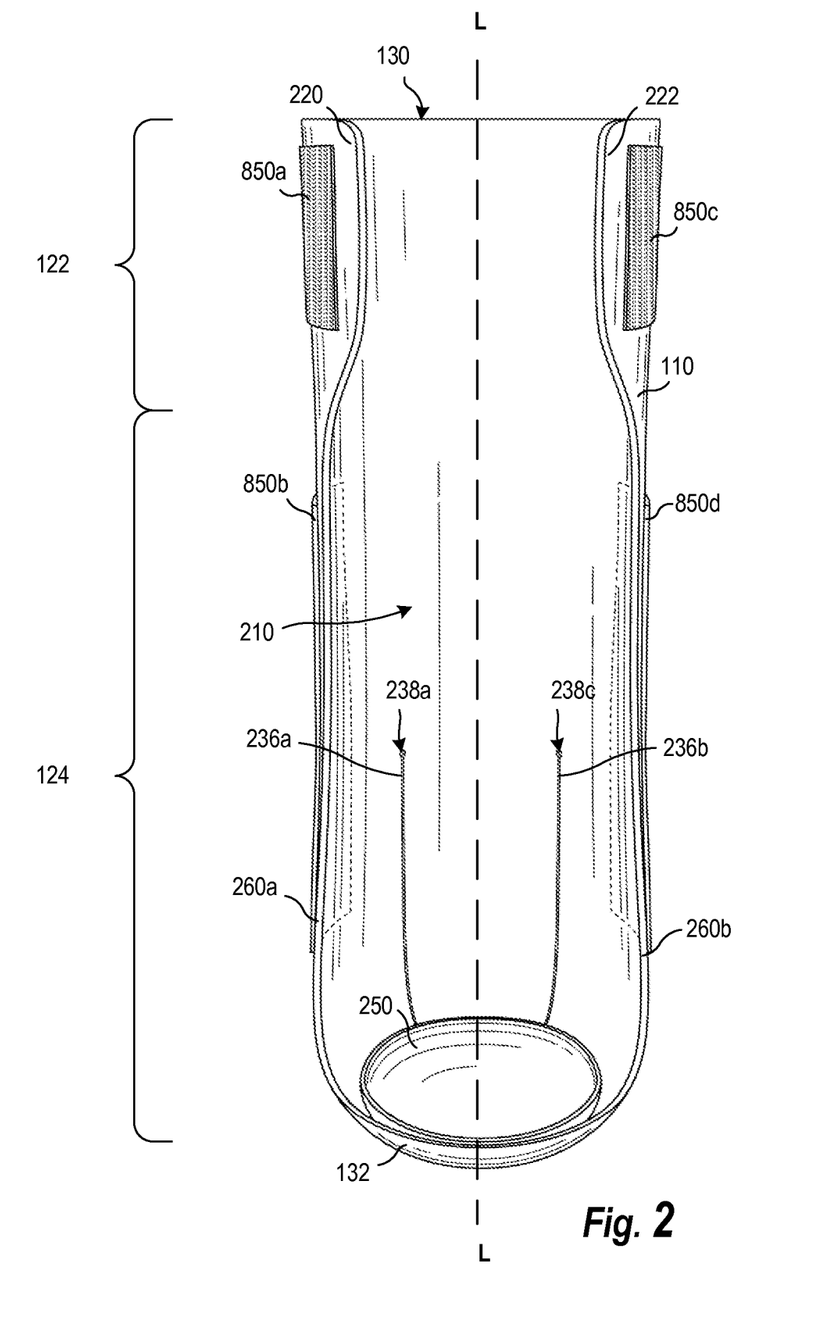
FIG. 2 is a front elevation view of a partially assembled residuum device as shown in FIG. 1A.

The posterior shell 110 comprises a proximal portion 122 and a distal portion 124 that extend along a longitudinal axis L of the posterior shell 110 (see also, FIG. 2). The posterior shell 110 is generally cylindrical in shape and includes an open end 130 positioned at the proximal portion of the posterior shell 110 and a closed end 132 positioned at the distal portion of the posterior shell 110. Although a closed distal end is shown and described herein, it will be understood that both ends may be open. The posterior shell 110 may have any length and diameter, which may be adjusted to fit the amputation residuum. In some embodiments, the posterior shell 110 is about 18 inches in length and about 5.5 inches in diameter along its length. The posterior shell 110 may have any thickness and the thickness may vary along the length of the proximal shell 110. For example, in some embodiments, the proximal portion 122 of the posterior shell 110 has a greater thickness in the proximal portion 122 than the distal portion 124.

Referring now to FIG. 2 the posterior shell defines an anterior opening 210 extending longitudinally from the proximal end for exposing the hollow interior of the posterior shell 110. In some embodiments, the width of the distal portion 124 of the anterior opening 210 defines a region that is about 40% of the circumference of the posterior shell 110. It will be understood that the width of the distal portion 124 of the anterior opening 210 may be more or less than about 40% of the circumference of the posterior shell 110 based on the desired rigidity or size of the posterior shell 110. The length of the anterior opening 210, in some embodiments, extends from the open end 130 to the closed end 132 along the longitudinal axis L of the posterior shell 110. In some embodiments, the proximal portion of the posterior shell 110 comprises a first ear 220 and a second ear 222 that extend circumferentially inwardly and are configured such that the width of the anterior opening 210 at the proximal portion 122 is less than the width of the anterior opening 210 at the distal portion 124.

In some embodiments, the posterior shell 110 is formed from a semi-rigid polymer material that is shaped to comfortably accommodate the posterior of a thigh, knee, and transtibial residuum following amputation below the knee. Examples of the semi-rigid polymer material include thermoplastics; polyolefins; plastics; ethylene vinyl acetate, polypropylene, polyethylene, polyethylene terephthalate, styrene, vinyl acetate, acrylonitrile, polyvinyl chloride, polyamide, silicone, rubber, and carbohydrates polymers or copolymers; cross-linked polymers or copolymers; and combinations thereof. The posterior shell, in some embodiments, is fabricated by thermo-forming the polymer material over a cylindrical model. In other embodiments, the posterior shell is formed by injection molding. The posterior shell 110 may be formed in any color or opacity. For example, the posterior shell 110 may be clear, slightly opaque, or completely opaque. In the case where the posterior shell 110 is clear or slightly opaque, the position of the floating pre-tibial shell 120 or any collecting fluids may be visible from the outside of the posterior shell 110. Similarly, anything positioned on the outside of the posterior shell 110, such as fabric fasteners 850a-d, may be visible from the inside. To enhance the comfort of the user, the inner surface of the posterior shell 110 may be lined. For example, the posterior shell 110 may include padding, wicking material, a gel layer, and the like.

Further shown in FIG. 2 is the circular pad 250 is disposed at the closed end of the proximal shell. The pad 250 may be formed from any soft, elastic, or conformable material. Examples of the material used in the pad 250 include sponge, plastazote, polypropylene terephthalate (PPT), foam, and the like.

Figure 3:
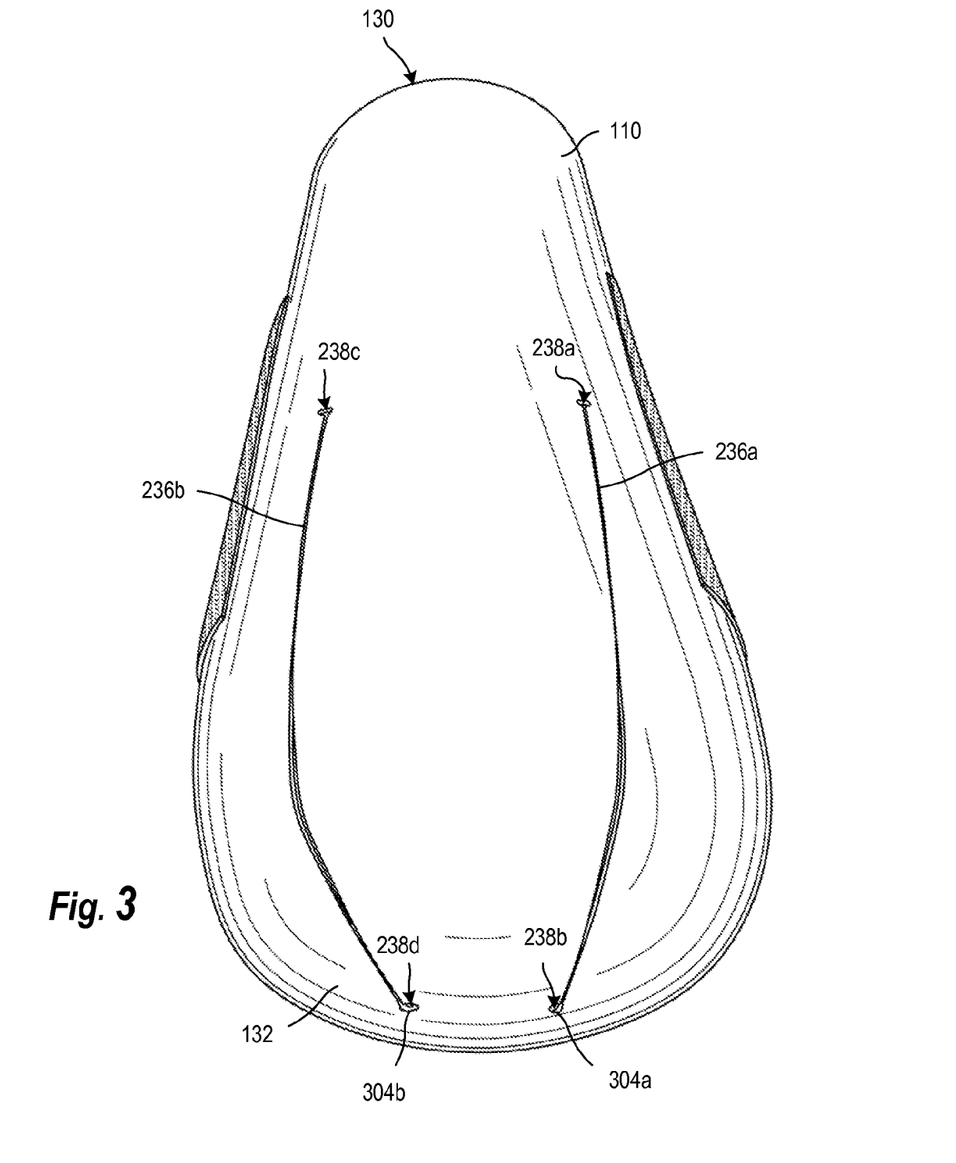
FIG. 3 is a rear perspective view of a portion of the residuum device according to some embodiments of the invention.
Figure 4:
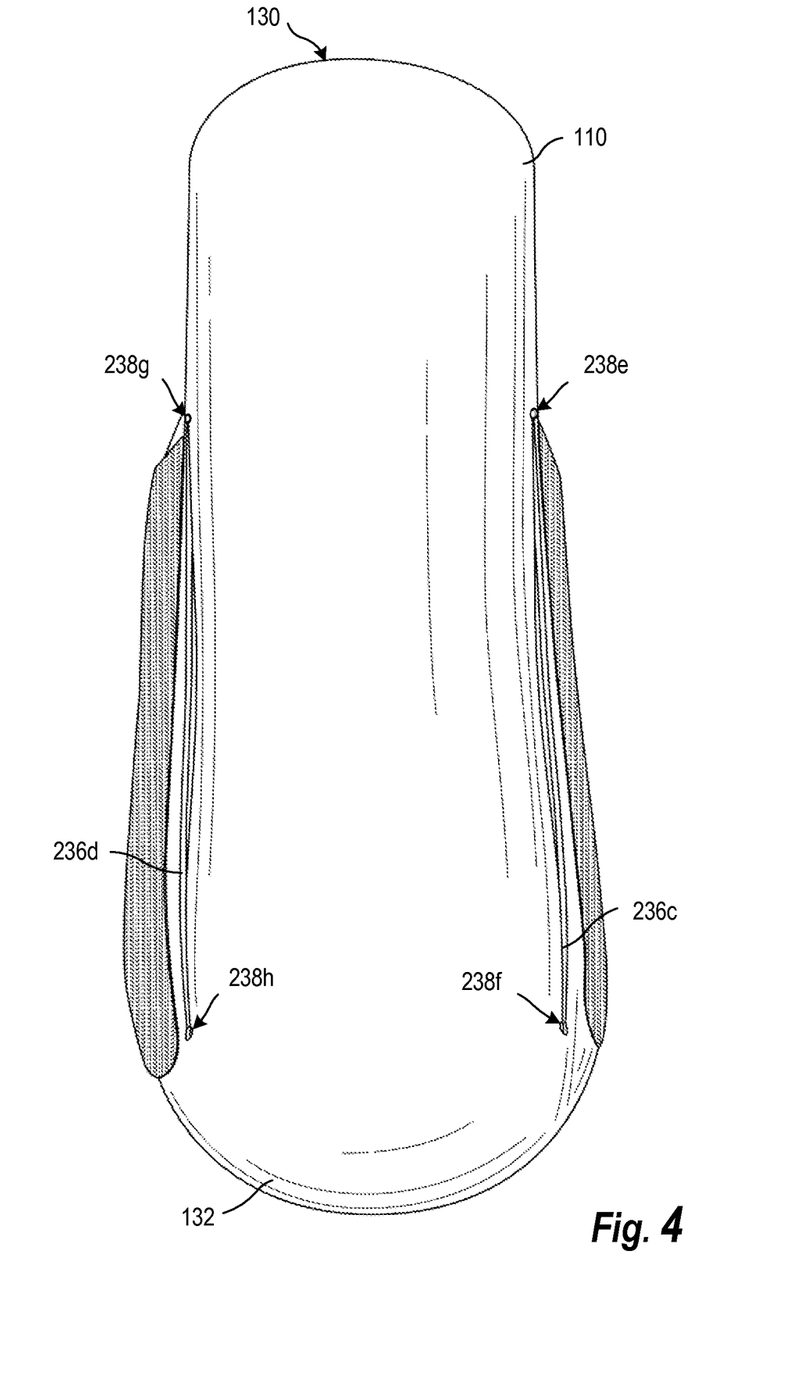
FIG. 4 is a rear perspective view of another embodiment of the residuum device.

Referring now to FIGS. 3 and 4, formed in the posterior shell 110 are a first slit 236a and a second slit 236b as shown in FIG. 3, and slits 236c and 236d shown in FIG. 4. The slits 236a, 236b or 236c, 236d allow for limited deformation of the shell to accommodate volume and diameter variances of the residuum within the posterior shell 110. The slits 236a-d may be formed by cutting the posterior shell 110 using a knife, saw, blade, die, punch, or the like. The slits 236a-d extend along the longitudinal axis of the posterior shell 110.

Each of the slits 236a-d includes a first end and a second end, the slits 236a-d having circular apertures 238a-h at each end (see, e.g., FIGS. 2-4). The slits 236a, 236b and 236c, 236d, as shown in FIG. 3 and FIG. 4, are formed in the posterior shell 110 and are positioned in parallel. The slits 236a and 236c are positioned about 1 inch to about 5 inches from a first side edge 260a and slits 236b and 236d are positioned about 1 inch to about 5 inches form a second side edge 260b of the posterior shell 110, where the side edges 260a, 260b extend along the longitudinal axis L of the posterior shell 110 (see, FIG. 2). The diameter of the circular apertures 238a-5h allows the gaps formed by the slits 236a-d to increase in width in response to an increase in residuum volume or diameter. The length of the slits and distance from the side edges may vary and any number of slits may be formed in the posterior shell 110 in accordance with the size of the residuum device 100 and volume and diameter fluctuations of the residuum.

In FIG. 3, at least a portion of the first slit 236a and the second slit 236b are positioned about 3 inches from the first side edge 260a and the second side edge 260b of the posterior shell 110, respectively. The slits 236a, 236b originate about 5 inches to about 12 inches from the open end 130. At the point of origin, the slits 236a, 236b are from about 2 inches to about 7 inches apart. In some embodiments, the slits 236a, 236b are about 3 inches apart at the point of origin. The slits 236a, 236b terminate at a first point 304a and a second point 304b, respectively. The points 304a, 304b are positioned about 0.5 inches to about 3 inches apart at the closed end 132 of the posterior shell 110. In some embodiments, the points 304a, 304b are positioned about 1.5 inches apart.

In FIG. 4, the slits 236c, 236d are about 1.5 inches from the first side edge 260a and the second side edge 260b of the posterior shell 110, respectively. The slits 236c, 236d originate about 5 inches to about 12 inches from the open end 130 and terminate near the closed end 132. The slits 236c, 236d run parallel along the longitudinal axis of the posterior shell 110 about 2 inches to about 7 inches apart.

Figure 5:
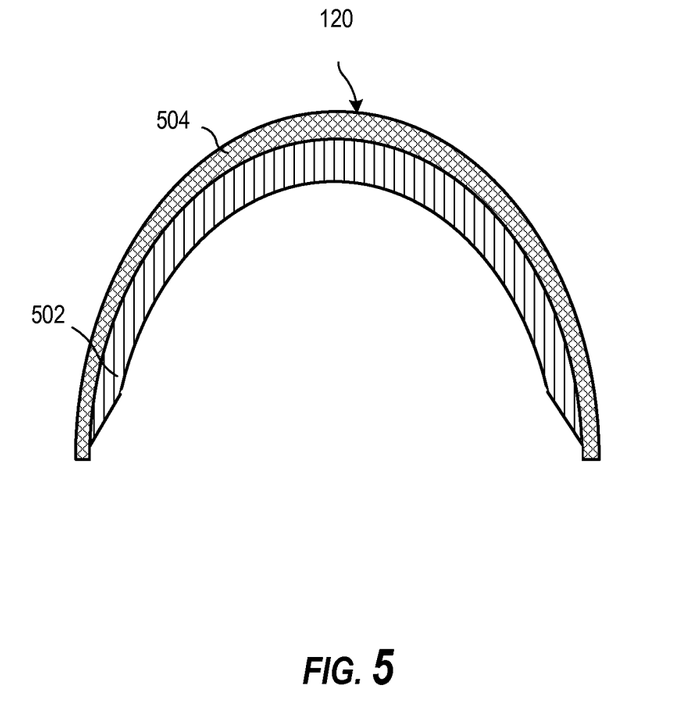
FIG. 5 is a cross-sectional view of the pre-tibial shell in FIG. 1B according to some embodiments of the invention.

Referring now to FIG. 5, the pre-tibial shell 120 includes an inner foam layer 502 positioned adjacent to an outer foam layer 504. In some embodiments, the inner foam layer 502 is laminated to the outer foam layer 504. The layers may be laminated using heat, adhesive, or a combination thereof. The laminated foam layers may then be cut to size, thermo-molded to a generally cylindrical model, and beveled along all edges. In other embodiments, the pre-tibial shell 120 is formed through an injection-molding process.

The inner foam layer 502 is positioned against the amputation residuum and, in some embodiments, comprises a soft material. The outer foam layer 504 comprises a rigid, high density material. This arrangement enhances the comfort and protection of the user's limb. The foam used in the pre-tibial shell 120 may be open cell foam, closed cell foam, polymer based foams, plant based foams, or combinations thereof. Examples of the inner foam layer 502 and outer foam layer 504 include: polyolefin, polyether, polyester, polyethylene, polypropylene, ethylene vinyl acetate, rubber, polyimide, vinyl chloride, polyurethane, styrene, carbon, soy, and cellulose based foams, and combinations thereof. The inner foam layer 502 and outer foam layer 504 may further include any number of additives or topical treatments such as antimicrobials, water resistant additives, coloring agents, and the like. Although two foam layers are illustrated in FIG. 5, it will be understood that the pre-tibial shell 120 may include only a single layer or any number of layers including additional foam layers or layers of other materials. For example, the pre-tibial shell 120 may include plastic, gel, fabric, and the like.

The pre-tibial shell 120 is configured to accommodate the shape of the amputation resdiuum and provide a secure and comfortable fit. As shown in FIG. 5, the thickness of the pre-tibial shell 120 varies. In some embodiments, the inner foam layer 502 has a beveled edge, tapering as it extends to the outer side edges of the pre-tibial shell 120. In other embodiments, the inner foam layer 502 tapers as it extends to the outer proximal and distal edges. As further shown in FIG. 5, the inner foam layer 502 has a greater thickness than the outer foam layer 504. It will be understood, however, that the inner foam layer 502 and outer foam layer 504 may have any thickness as long as the pre-tibial shell 120 fits securely against the amputation residuum. As best shown in FIGS. 1A and 1B, an upper portion adjacent the proximal end of the pre-tibial shell 120. The upper portion defines an inner indentation for receiving a knee of the user limb when a leg is amputated below the knee.

Figure 6:
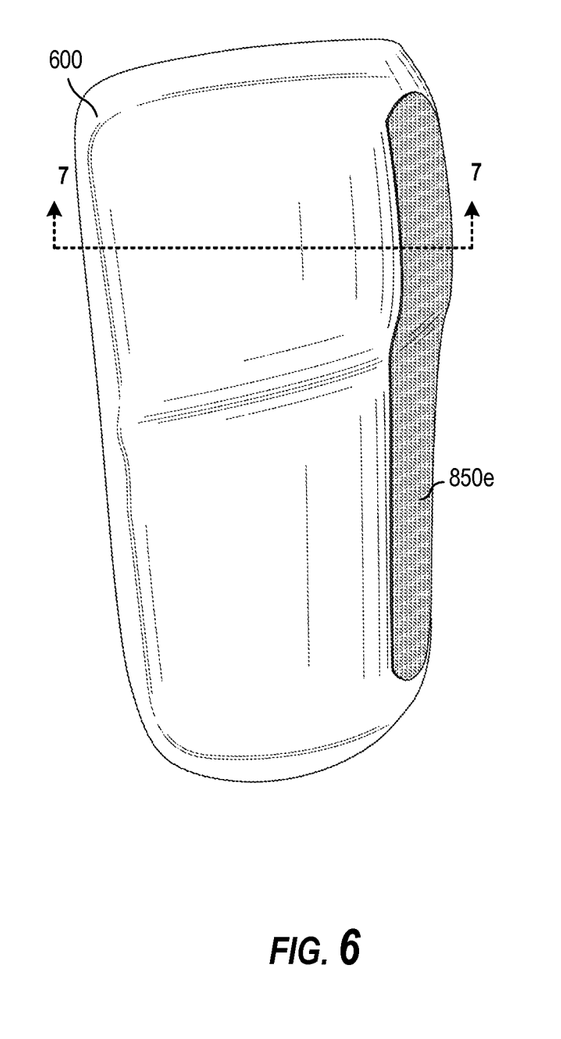
FIG. 6 is another embodiment of a pre-tibial shell.

FIG. 6 illustrates another embodiment of a pre-tibial shell 600 of the residuum device 100, which may be used in conjunction with the posterior shell 110. The pre-tibial shell 600 can be included in the residuum device 100 and may be used in conjunction with the posterior shell 110. The pre-tibial shell 600 includes a fastener strip 850e that is positioned on at least a portion of an outer foam layer 704.

Figure 7:
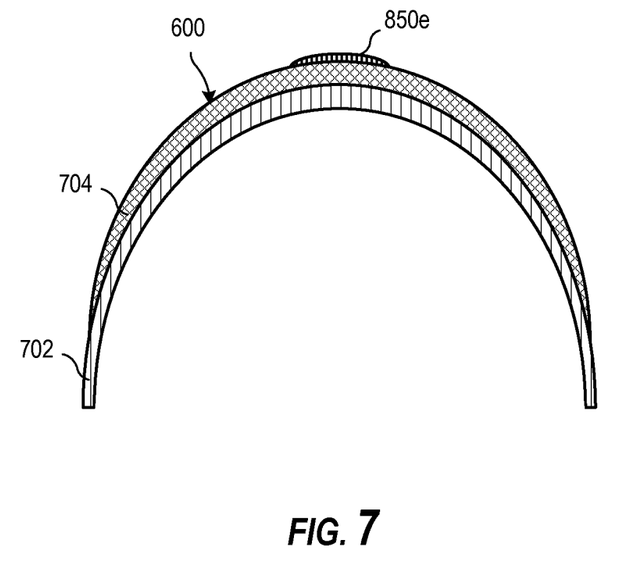
FIG. 7 is a cross-sectional view of the pre-tibial shell in FIG. 6 according to some embodiments of the invention.

Referring to FIG. 7, the pre-tibial shell 600 comprises an inner foam layer 702 and an outer foam layer 704. In some embodiments, the outer foam layer 704 tapers inwardly as it extends toward the outer edges of the pre-tibial shell 120 such that only the inner foam layer 702 extends along the outer perimeter of the pre-tibial shell 600. In other embodiments, the width of the upper portion adjacent the proximal end of the pre-tibial shell 600 is wider than the lower portion adjacent the distal end of the pre-tibial shell 600.

Both embodiments of the pre-tibial shell 120, 600 may be modified in any way. For example, the pre-tibial shell 120, 600 may be easily trimmed or cut with scissors to better fit the user's limb.

Figure 8:
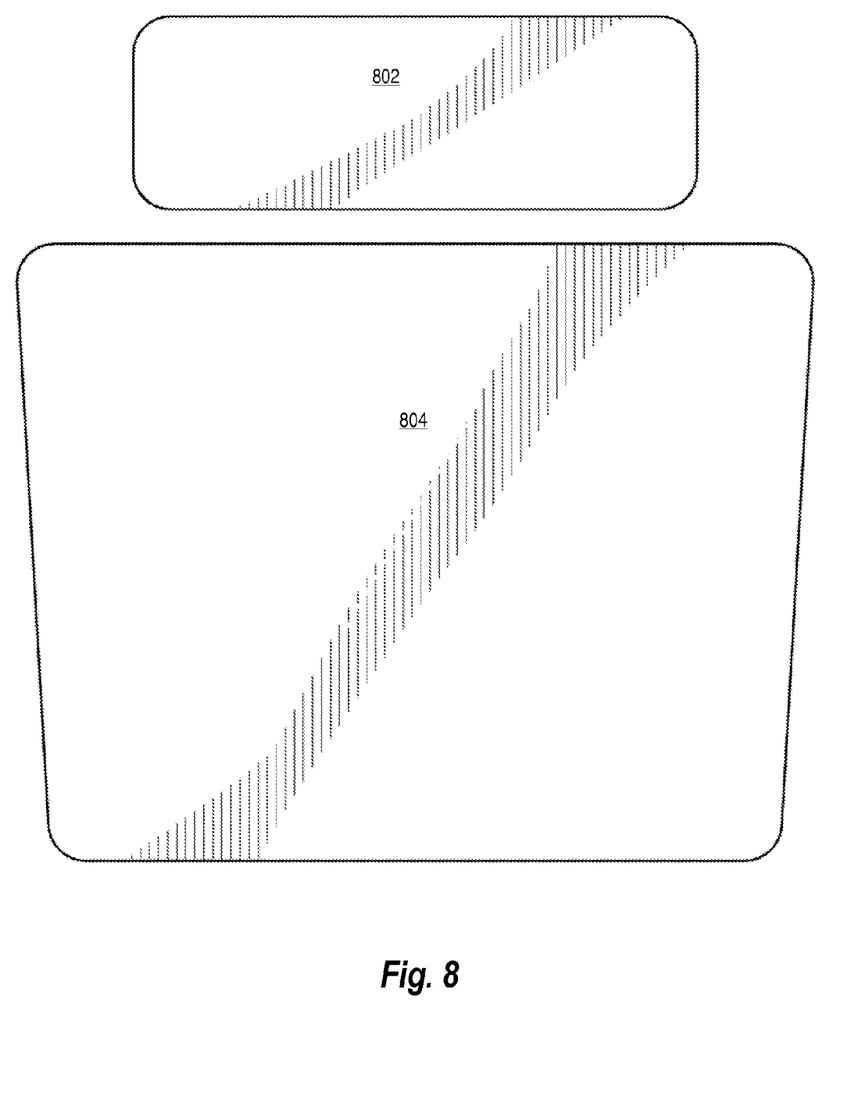
FIG. 8 is a top plan view of enclosure panels for a residuum device according to some embodiments of the invention.
Figure 9:
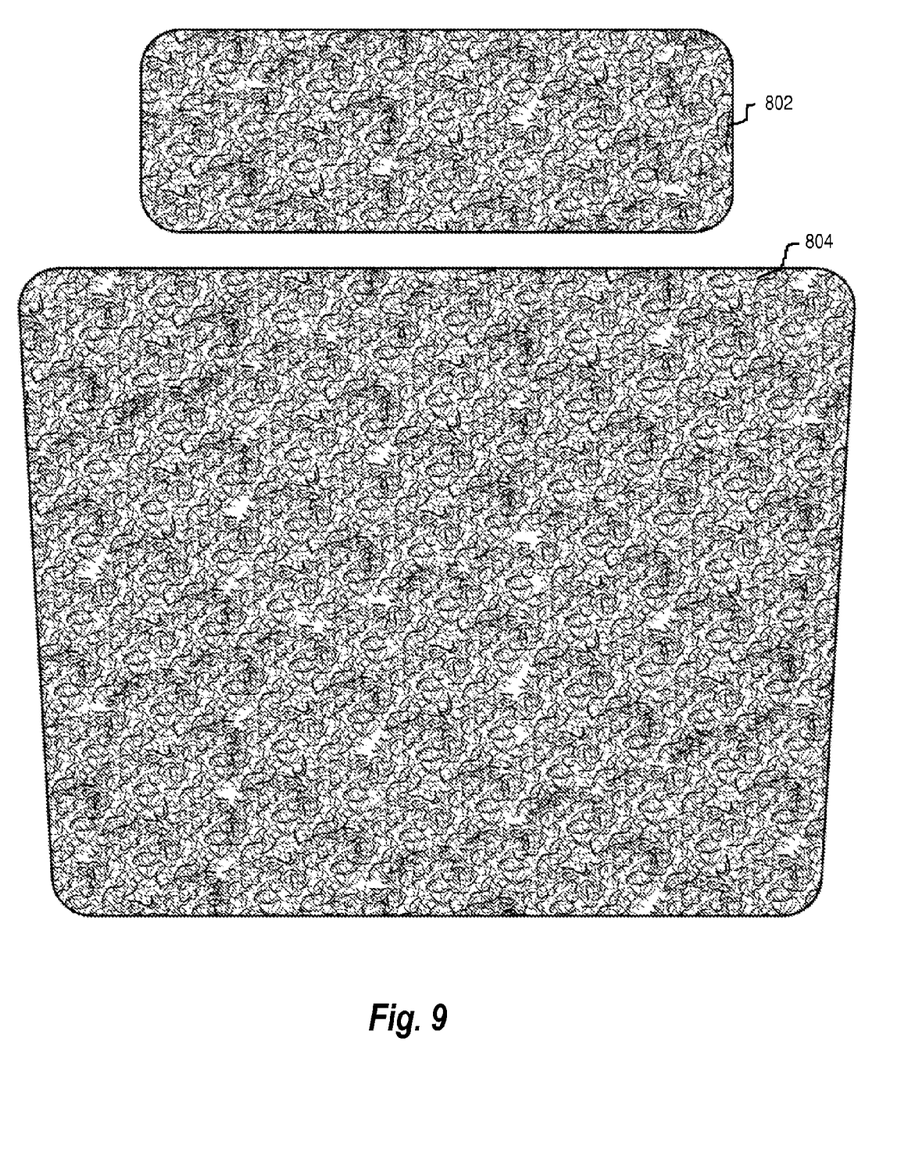
FIG. 9 is a rear plan view of the enclosure panels of FIG. 8.

FIGS. 8 and 9 illustrate an enclosing means 800 for enclosing an amputation residuum within the interior of the posterior shell 110. The enclosing means 800 includes a first enclosure panel 802, and optionally, a second enclosure panel 804. The enclosure panels 802, 804 may be formed in any shape. In the illustrated embodiments, the first enclosure panel 802 is rectangular and the second enclosure panel 804 is trapezoidal. The rear portions of the enclosure panels 802, 804 comprise soft fuzzy or a "loop" type of fabric such that the rear potions may adhere to the fastener strips 850a-e (FIG. 9). The enclosure panels 802, 804 may come in any color, size, shape, width, length, area, and thickness. In the illustrated embodiments, the enclosure panels 802, 804 are rectangular in shape. In other embodiments, the enclosure panels 802, 804 are 11 inches by 20 inches. The dimensions of enclosure panels 802, 804 may be modified by trimming the panels. Although two enclosure panels 802, 804 are illustrated, it will be understood that a single enclosure panel or additional panels may be provided. The enclosure panels 802, 804 are placed over the fastener strips 850a-e to keep the enclosing means 800 in place. The enclosure panels 802, 804, in some embodiments, include one or more layers of fabric, foam, padding, rubber, neoprene, elastic material, and the like. The enclosure panels 802, 804 may be formed by cutting, die-cutting, or stamping the panels from a roll of material. Other types of fastening systems may also be used with the residuum device 100 such as clamps, straps, belts, tapes, and the like.

Figure 10:
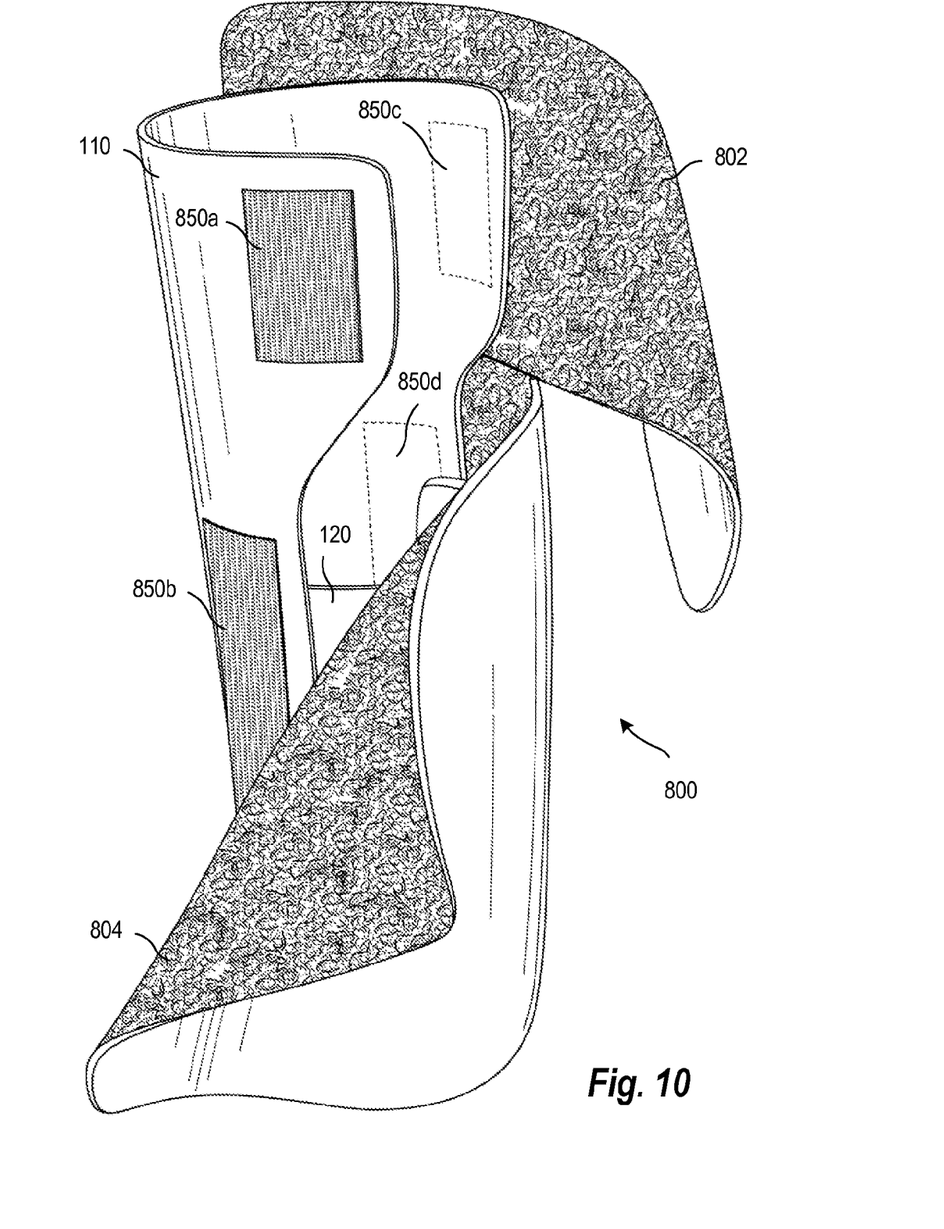
FIG. 10 is a perspective view of an enclosing means and a residuum device according to some embodiments of the invention.

In FIG. 10, the residuum device 100 is further illustrated including the enclosing means 800. One or more of the enclosure panels 802, 804, in some embodiments, are positioned across the patella to enhance control over knee flexion. In some embodiments, the enclosure panels 802, 804 and the fastener strips 850a-e comprise fabric made of fastening material, such as hook and loop type fasteners (e.g., "Velcro"). Referring to FIGS. 1A and 1B, the fastener strips 850a-d are positioned on at least a portion of the outer surface of the posterior shell 110. The fastener strips 850a and 850c are positioned on the first ear 220 and the second ear 222, respectively. The fastener strips 850b and 850d are positioned on the outer surface of the posterior shell 110 in the distal portion 124. As described herein above, the second embodiment the pre-tibial shell 600 may also include a fastener strip 850e that is positioned on the outer surface of the pre-tibial shell 120.

The residuum device 100 can be used to accommodate an amputation residuum. In use, the posterior shell 110 is applied to the posterior of a patient's thigh and residual limb by positioning at least a portion of the residuum into the hollow interior of the posterior shell 110. As the posterior aspect of the posterior shell 110 is a continuous shell, the residuum device 100 will complete a three point pressure configuration comprised of posterior thigh, anterior patella, and posterior tibia in order to provide a knee extension load. In some embodiments, the proximal potion 122 extends along at least a portion of the user's thigh and the distal portion 124 extends along at least a portion of the user's tibia. Depending on the length of the amputation residuum, the posterior shell 110 may, for example, be trimmed at the open end 130.

The residual limb may be further accompanied by postoperative dressings. The relative position of the posterior shell 110 to the residuum is such that the distal end of the residuum engages a pad placed in the closed end 132 of the residuum device 100. The slits 236a, 236b or 236c, 236d formed in the posterior shell 110 are configured to expand to avoid over-compressing an often painful postoperative residuum. The circular apertures 238a-h positioned at the ends of the longitudinal slits 236a-d cause the slits 236a-d formed in the posterior shell 110 to widen in response to volume and diameter variations in the amputation residuum.

It will be understood that the residuum device 100 may be used with or without the pre-tibial shell 120, 600 depending on the needs or condition of the patient. In use, the pre-tibial shell 120 or 600 is positioned in the anterior opening 210 of the posterior shell 110 such that the pre-tibial shell 120, 600 comes in contact with the anterior aspect of the amputation residuum. In an application where amputation is below the knee, the pre-tibial shell 120, 600 is positioned such that the distal end of the posterior shell 110 is adjacent the distal end of the residuum and extending upwardly to the patella.

For a shorter trans-tibial residuum, the pre-tibial shell 120, 600 may be trimmed for removing material from its distal end such that the pre-tibial shell 120, 600 is positioned more distally. The pre-tibial shell 120, 600 is tucked into the posterior shell in order to appropriately accommodate for volume loss secondary to edema reduction within the residuum. For example, in some embodiments, at least a portion of the posterior shell 110 defining the anterior opening 210 overlaps at least a portion of the peripheral edges of the pre-tibial shell 120, 600. This allows the posterior shell 110, when expanding or contracting in response to volume and diameter variances in the amputation residuum, to move relative to outer foam layer 504 of the pre-tibial shell 120, 600. When the pre-tibial shell 120, 600 is adjacent to the amputation residuum exposed through the anterior opening 210, the pre-tibial shell 120, 600 floats to accommodate the amputation residuum as it expands and contracts while it simultaneously stabilizes the amputation residuum.

In some embodiments, the user's residuum is enclosed in the proximal portion 122 of the posterior shell 110 by fastening the first enclosure panel 802 to the posterior shell 110 over the anterior of the patient's thigh. And the user's residuum is enclosed in the distal portion 124 of the posterior shell 110 by fastening the second enclosure panel 804 to the distal portion 124 of the posterior shell 110 and over the pre-tibial shell 120, 600 that has been appropriately applied to the anterior of the user's residuum.

The residuum device 100 can be used in conjunction with any number of additional items such as foam padding, a prosthetic sock or prosthetic shrinker, straps, strapping apparatus and belt (e.g., fork strap and suspension belt), and the like. In particular, the strapping apparatus and belt is useful when a user is upright, standing, or ambulating, and the prosthetic sock can be used to further protect the residuum and accommodate volume variance within the residuum. In some embodiments, a kit is provided. The kit comprises one or more of the posterior shells 110, pre-tibial shells 120, 600, and enclosure panels 802, 804. In other embodiments, the kit comprise packaging, a container, instructions, labels, foam padding, a prosthetic sock or prosthetic shrinker, straps, a strapping apparatus, and the like.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. For example, while the residuum device 100 is described herein for use with a leg, it will be understood that the residuum device 100 may also be used for an arm or other body part. Therefore, it is to be understood that, within the scope of the appended claims, the invention may be practiced other than as specifically described herein.

The invention claimed is:

1. An apparatus for post amputation residuum maintenance, the apparatus comprising:
    an elongated shell having a longitudinal axis and defining a hollow interior closed at a distal end, the shell having an opening extending from a proximal end and adapted to receive a residuum into the interior of the shell, and a longitudinal slit having a circular aperture at each end; and
    a second shell having a longitudinal axis and substantially arcuate in a cross-section taken transverse to the longitudinal axis of the second shell,
    the second shell adapted to be positioned adjacent to the residuum and configured to cover at least a portion of the opening of the shell,
    wherein the second shell comprises:
    an inner foam layer comprising a soft material; and
    an outer foam layer comprising a rigid material, wherein the outer layer is positioned
    adjacent to the inner foam layer.

2. The apparatus of claim 1, wherein the peripheral edge of the inner foam layer tapers outwardly.

3. The apparatus of claim 1, wherein the peripheral edge of the outer foam layer tapers inwardly.

4. A method for post amputation residuum maintenance, the method comprising:
    providing an elongated shell having a longitudinal axis and defining a hollow interior closed at a distal end, the shell having an opening extending from a proximal end and adapted to receive a residuum into the interior of the shell, and a longitudinal slit having a circular aperture at each end;
    positioning a residuum in the interior of the shell via the opening;
    providing a second shell adapted to be positioned adjacent to the residuum, the second shell configured to cover at least a portion of the opening;
    positioning the second shell over at least a portion of the residuum exposed through the opening in the shell; and adjusting the position of the second shell to fit against the residuum, wherein at least a portion of an edge of the first shell defining the opening partially overlaps the second shell.

* * * * *